(12) United States Patent
Geffen et al.

(10) Patent No.: US 11,931,017 B2
(45) Date of Patent: Mar. 19, 2024

(54) ACTUATION CONNECTOR FOR A TOOL

(71) Applicant: VALUEBIOTECH ISRAEL LTD., Herzliya (IL)

(72) Inventors: Nir Geffen, Ramat HaSharon (IL); Avraham Rami Lore, Kiryat Tivon (IL); Eldar Cohen, Yokneam Elite (IL); Alexander Mikler, Rehovot (IL); Paul Price, Nes Tziona (IL); Antonello Forgione, Milan (IT); Renzo Zaltieri, Milan (IT)

(73) Assignee: VALUEBIOTECH ISRAEL LTD., Ness Ziona (IL)

( * ) Notice: Subject to any disclaimer, the term of this patent is extended or adjusted under 35 U.S.C. 154(b) by 701 days.

(21) Appl. No.: 16/972,143

(22) PCT Filed: Jun. 4, 2019

(86) PCT No.: PCT/IB2019/054640
§ 371 (c)(1),
(2) Date: Dec. 4, 2020

(87) PCT Pub. No.: WO2019/234629
PCT Pub. Date: Dec. 12, 2019

(65) Prior Publication Data
US 2021/0361271 A1    Nov. 25, 2021

(30) Foreign Application Priority Data

Jun. 4, 2018 (IL) .......................................... 259813
Jun. 4, 2018 (IL) .......................................... 265002

(51) Int. Cl.
*A61B 50/30*    (2016.01)
*A61B 17/00*    (2006.01)

(52) U.S. Cl.
CPC ........ *A61B 17/00234* (2013.01); *A61B 50/30* (2016.02); *A61B 2017/00314* (2013.01);
(Continued)

(58) Field of Classification Search
CPC ............ A61B 1/0014; A61B 17/00234; A61B 2017/00296; A61B 2017/003;
(Continued)

(56) References Cited

U.S. PATENT DOCUMENTS 7,297,142 B2    11/2007 Brock
2007/0270640 A1    11/2007 Dimitriou et al.
(Continued)

FOREIGN PATENT DOCUMENTS

EP    2772210 A2    9/2014
WO    2018/034965 A1    2/2018

OTHER PUBLICATIONS

Extended European Search Report received for EP Serial No. EP19814920 dated Apr. 3, 2023, 8 pgs.
(Continued)

*Primary Examiner* — George Manuel
(74) *Attorney, Agent, or Firm* — Merchant & Gould P.C.

(57) ABSTRACT

A tool actuation connector includes a tool activation interface, a longitudinal lock interface and a rotation lock interface. The tool actuation connector includes a latching spring, an inner sleeve and an outer sleeve. The latching spring includes a plurality of spring hooks, for coupling with the tool activation interface. The inner sleeve is operable to longitudinally move relative to the latching spring. The inner sleeve couples the latching spring to the activation interface when the inner sleeve is located over the latching spring and releases the latching spring from the activation interface when the inner sleeve moves away from the latching spring toward the proximal direction. The outer sleeve is rotation-
(Continued)

ally locked with the inner sleeve and is operable to longitudinally move relative to the inner sleeve. The outer sleeve is further operable to rotationally lock with the tool via the rotation lock interface.

20 Claims, 13 Drawing Sheets

(52) U.S. Cl.
CPC .............. *A61B 2017/00389* (2013.01); *A61B 2017/00464* (2013.01); *A61B 2017/00473* (2013.01); *A61B 2017/00477* (2013.01)

(58) Field of Classification Search
CPC ........... A61B 2017/00314; A61B 2017/00362; A61B 2017/00389; A61B 2017/00464; A61B 2017/00473; A61B 2017/00477; A61B 2017/2906; A61B 2017/2931; A61B 2017/294; A61B 50/30; A61B 90/50

See application file for complete search history.

(56) References Cited

U.S. PATENT DOCUMENTS

| | | |
|---|---|---|
| 2008/0004656 A1 | 1/2008 | Livneh |
| 2008/0021278 A1 | 1/2008 | Leonard |
| 2009/0221873 A1 | 9/2009 | McGrath |
| 2011/0295242 A1 | 12/2011 | Spivey et al. |
| 2013/0066304 A1 | 3/2013 | Belson |
| 2013/0184690 A1* | 7/2013 | Doyle .................... A61B 34/70 606/1 |
| 2016/0066999 A1 | 3/2016 | Forgione et al. |
| 2016/0175060 A1 | 6/2016 | Park |
| 2018/0110572 A1 | 4/2018 | Flatt |

OTHER PUBLICATIONS

International Search Report and Written Opinion for PCT/IB2019/054640, dated Nov. 7, 2019.

* cited by examiner

ACTUATION CONNECTOR FOR A TOOL

This application is a National Stage application of PCT/IB2019/054640, filed Jun. 4, 2019, which claims priority to Israeli Patent Application No. 259813, filed Jun. 4, 2018, and Israeli Patent Application No. 265002, filed Jun. 4, 2018, which applications are incorporated herein by reference. To the extent appropriate, a claim of priority is made to each of the above-disclosed applications.

FIELD OF THE DISCLOSED TECHNIQUE

The disclosed technique relates to tools in general in general, and to tool mechanism, in particular.

BACKGROUND OF THE DISCLOSED TECHNIQUE

In many technological fields, different tools are employed to perform different operations. In the medical field, and specifically in the surgical filed, the different tools may included forceps, needle drivers, scissors, scalpels and the like. Often, it may be required to change a tool during operation (e.g., surgery).

U.S. Pat. No. 7,297,142 to Brock, entitled "Interchangeable Surgical Instrument" directs to interchangeable surgical instrument in which a magazine of tools is positioned outside the body. The tool is held within the magazine. The engagement hooks of the tool are spring biased outwardly in an open configuration. To engage the tool driver with the tool, the tool driver is pushed against the tool. As the tool starts to move within the passage, the walls of passage press against the engagement hooks until the engagement hooks lock with the driver hooks.

U.S. Patent Application Publication 2013/0184690 to Doyle, entitled "Systems, Apparatuses and Methods of Tool, Exchange" directs to engaging and disengaging of an end tool, with an holster or tool exchange device, may be accomplished by moving the instrument to which the end tool is attached sequentially along two motions, a first motion and a second motion. Each motion may be bi-directional and the two directions may be used to perform engaging and/or disengaging operations as described below. The first motion occurs along linear path, and the second motion is in rotational path. Moving the instrument along the first and then the second motion will: 1) engage the end tool with the holster via a tool engaging system components 2) engage an instrument via the holster further via operating instrument engaging features operable with holster, 3) allow the end tool to be disconnected from the instrument and features operable with holster, and 4) disengage the instrument from the holster. The instrument may then be moved in the reverse of the first motion direction along path to allow the instrument to be moved independently of the holster. Moving the instrument again in the first and then the second motion will: 1) engage the instrument with the holster, 2) allow the end tool to be connected to the instrument, and, upon moving again in the first direction allow the instrument to disengage from the holster with the engaged end tool connected, and allow the instrument and end tool to be used as a unit.

U.S. Patent Application Publication 2007/0270640 to Dimitriou et al, entitled "Endoscope Tool Coupling" directs to a connector apparatus attachable to the proximal end of an endoscope, through which tool can be inserted or extracted from the endoscope. The connector apparatus includes a connector body that has a plurality of fingers that are configured to engage and securely lock onto a port of the endoscope. The connector body locks onto the port with a connector nut that is threaded on the connector body to tighten or loosen the connector fingers from the endoscope port mount. The endoscope includes fingres which rotationally lock the connector apparatus with the endoscope.

U.S. Patent Application Publication 2009/0221873A1 to McGrath directs to an adaptor to orient an elongate medical device in relation to an endoscope. The adaptor includes a first portion and a second portion. The distal end of the first portion is connected and rotationally secured to an endoscope at the proximal end thereof. The first portion includes a first lumen longitudinally therethrough either an orienting key or a keyway extending longitudinally at least partially there along the first portion. The second portion connects with the first portion and includes a second lumen extending longitudinally therethrough. The second portion connects with the first lumen and also includes a key or the keyway extending longitudinally at least partially there along. The keyway configured to releasably mate with the key to orient and rotationally secure the second portion relative to the first portion. A medical device is inserted through the second portion while being and rotationally secured relative to the second portion. When the medical device is inserted through the endoscope, the adaptor orients the tip thereof relative to the distal portion of the endoscope portion.

SUMMARY OF THE PRESENT DISCLOSED TECHNIQUE

It is an object of the disclosed technique to provide a novel tool actuation connector. In accordance with the disclosed technique, there is thus provided a tool actuation connector, where the tool includes a tool activation interface, a longitudinal lock interface and a rotation lock interface. The tool actuation connector includes a latching spring, an inner sleeve and an outer sleeve. The latching spring includes a plurality of spring hooks, for coupling with the tool activation interface. The inner sleeve is operable to longitudinally move relative to said latching spring. The inner sleeve couples the latching spring to the activation interface when said inner sleeve is located over said latching spring and releases the latching spring from the activation interface when the inner sleeve moves away from the latching spring toward the proximal direction. The outer sleeve is rotationally locked with the inner sleeve and is operable to longitudinally move relative to the inner sleeve. The outer sleeve is further operable to rotationally lock with said tool via said rotation lock interface.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a tool actuation connector mechanism, for connecting with a selected tool or to release the tool which is employed, during operation (e.g., surgery). In other words, the tool mechanism according to the disclosed technique enables exchanging tools of a tool guide during operation. The tool actuation connector includes a tool activation interface, a longitudinal lock interface and a rotation lock interface. The actuation connector includes a latching spring, an inner sleeve and an outer sleeve. The latching spring includes a plurality of spring hooks, for coupling with the tool activation interface. The inner sleeve is operable to longitudinally move relative to said latching spring. The inner sleeve couples the latching spring to the activation interface when said inner sleeve is located over said latching spring and releases the latching spring from the activation interface when the inner sleeve moves away from the latching spring toward the proximal direction. The outer sleeve is rotationally locked with the inner sleeve and is operable to longitudinally move relative to the inner sleeve. The outer sleeve is further operable to rotationally lock with said tool via said rotation lock interface.

Figure 1A:
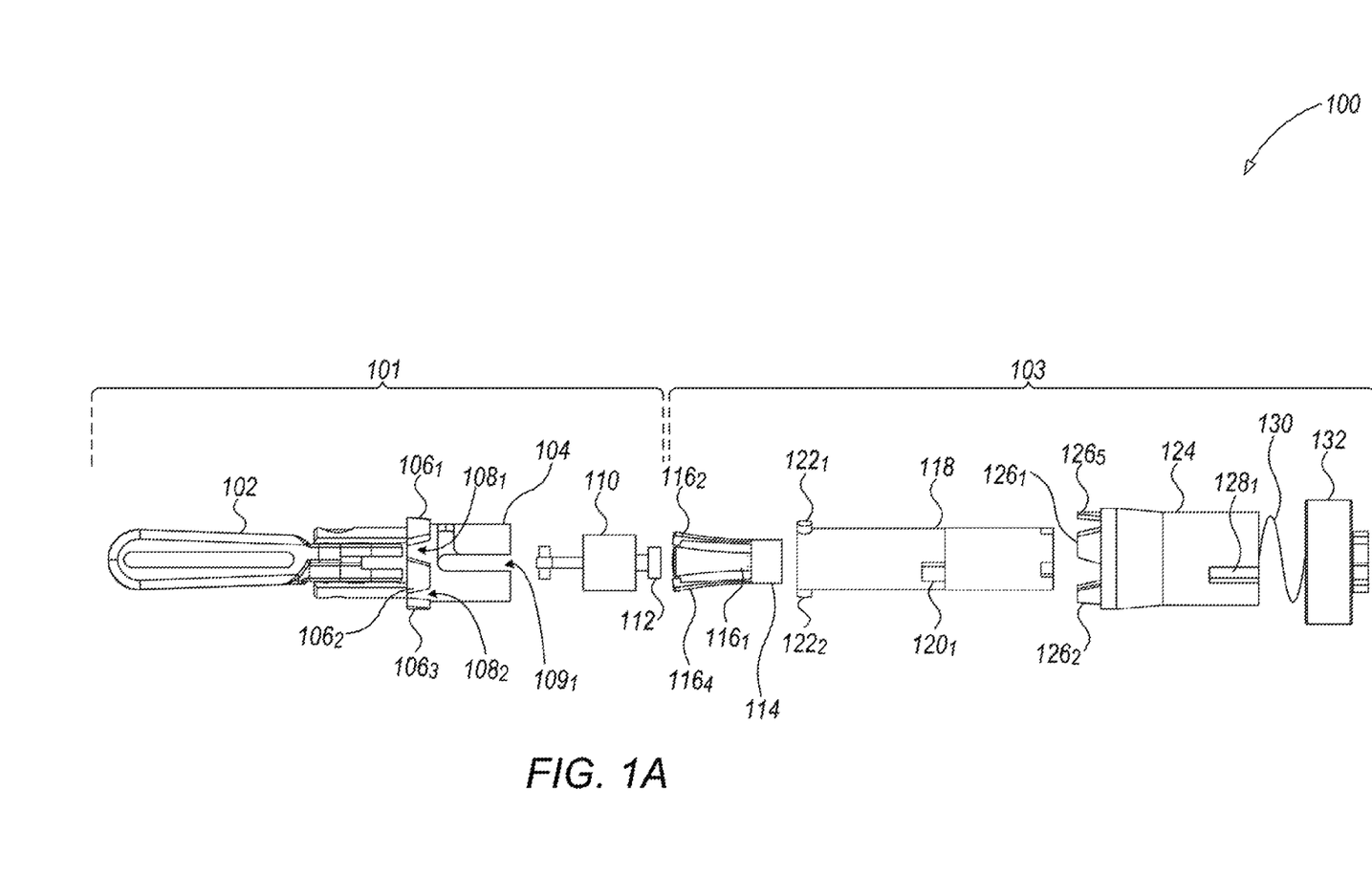
FIGS. 1A and 1B depict the components of tool mechanism in accordance with an embodiment of the disclosed technique.
Figure 1B:
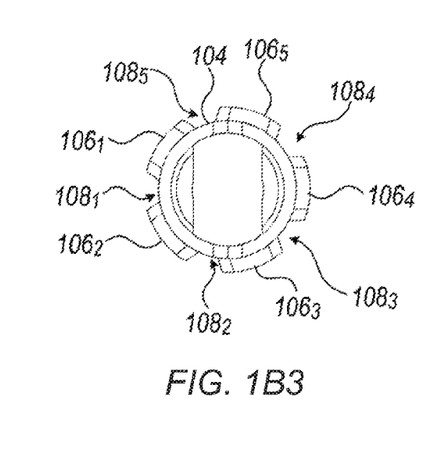
FIGS. 1C-1E depict a tool mechanism in an assembled and connected state in accordance with an embodiment of the disclosed technique.
FIGS. 1F-1I depict the process of releasing actuation connector from a tool section in accordance with an embodiment of the disclosed technique.
Figure 1B:
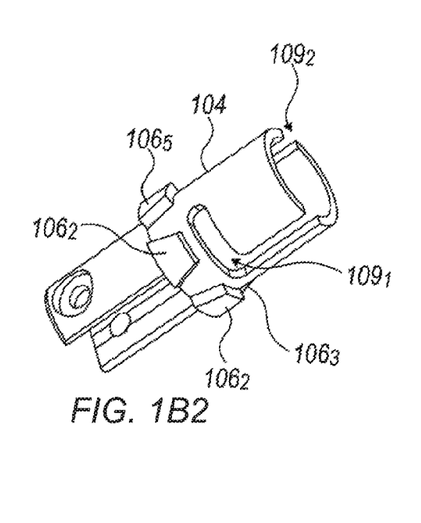
Figure 1B:
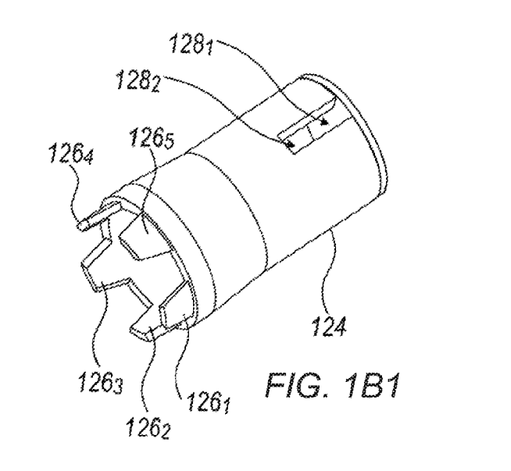
Figure 1B:
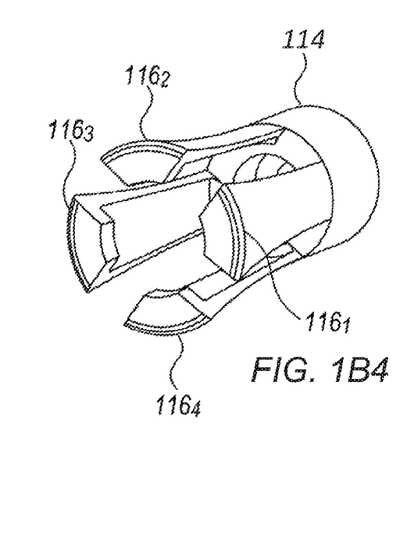
Figures 1B, 1B:
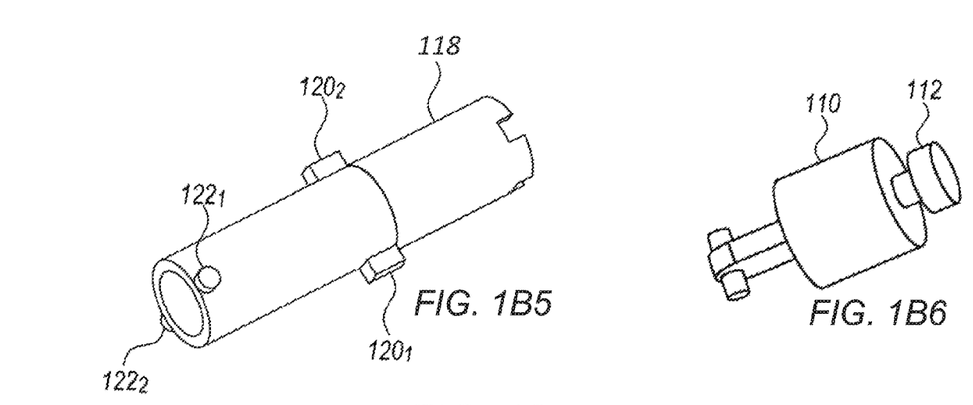
Figure 1C:
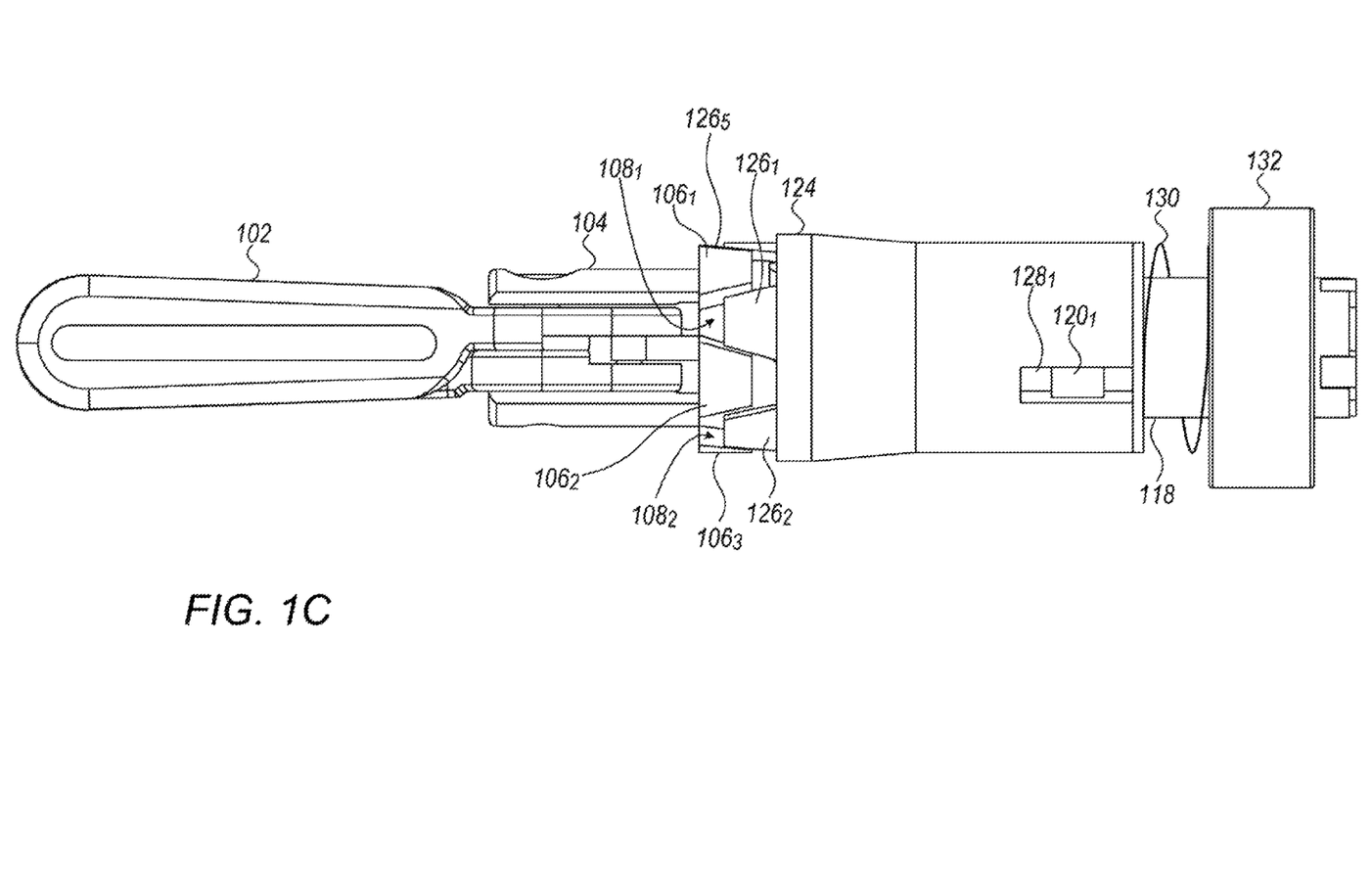
Figure 1D:
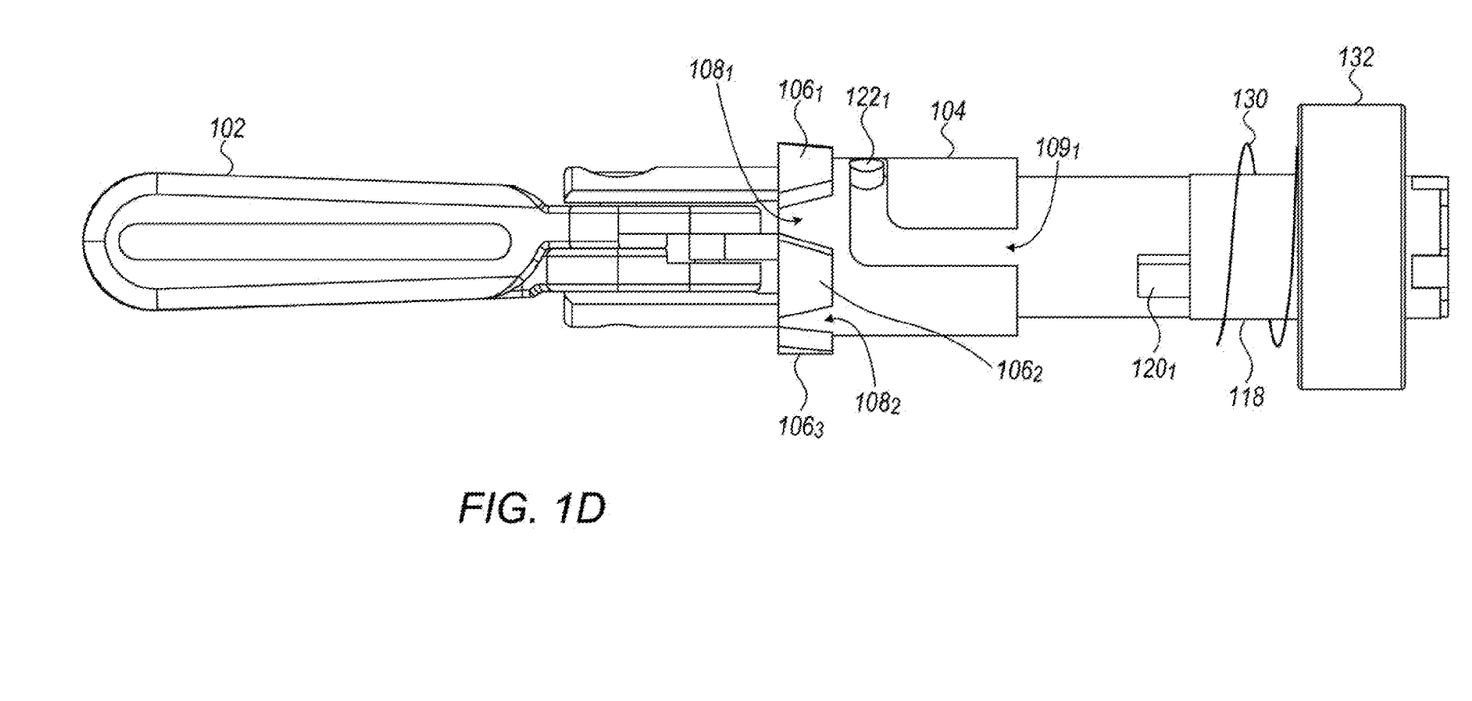

Reference is now made to FIGS. 1A-1I, which are schematic illustrations of a tool mechanism, generally referenced 100, constructed and operative in accordance with an embodiment of the disclosed technique. Tool mechanism 100 includes a tool section 101 and an actuation connector 103. FIGS. 1A and 1B depict the components of tool mechanism 100. FIG. 1C-1D depicts tool mechanism 100 in an assembled and connected state. FIGS. 1E-1I depicts the process of releasing actuation connector 103 from tool section 101.

For the sake of the description which follows, the direction toward the tool section 101 is referred to as 'distal direction' or 'distal end' and the toward actuation connector 103 is referred to as 'proximal direction' or 'proximal end'. Tool section 101 includes a tool 102, a tool housing 104 and a tool activation interface such as a push-pull rod 110. Tool housing 104 includes a rotation lock interface. In exemplary tool mechanism 100, the rotation lock interface includes a plurality of rotation lock protrusions at the distal end thereof. In exemplary too mechanism 100 tool housing 104 includes five rotation lock protrusions $106_1$, $106_2$, $106_3$, $106_4$ and $106_5$. Rotation lock protrusions $106_1$-$106_5$ create a plurality of tool rotation lock grooves $108_1$, $108_2$, $108_3$, $108_4$ and $108_5$. Tool housing 104 includes at a longitudinal lock interface. In the example brought forth in FIGS. 1A-1I, longitudinal lock interface is in the form of two L-shaped cutouts $109_1$ and $109_2$. Each one of L-shaped cutouts $109_1$ and $109_2$ includes a longitudinal section and a lateral section. Push-pull rod 110 includes a mushroom pin 112.

Actuation connector 103 includes a latching spring 114, an inner sleeve 118 and an outer sleeve 124. Latching spring 114 includes a plurality of spring hooks. In the example brought forth in FIGS. 1A-1I latching spring 114 includes four spring hook $116_1$, $116_2$, $116_3$ and $116_4$. Inner sleeve 118 includes at least one sleeve rotation lock pin and at least one sleeve longitudinal lock pin. In exemplary tool mechanism 100, inner sleeve 118 includes two sleeve rotation lock pins $120_1$ and $120_2$ and two sleeve longitudinal lock pin $122_1$ and $122_2$. Outer sleeve 124 includes a plurality of rotation lock teeth at the distal end thereof and at least one sleeve rotation lock groove. In exemplary tool mechanism 100, outer sleeve 124 includes five rotation lock teeth $126_1$, $126_2$, $126_3$, $126_4$ and $126_5$ extending from said inner sleeve toward the distal direction. Outer sleeve 124 two sleeve rotation lock grooves $128_1$ and $128_2$ located on the lateral surface of outer sleeve 124. Tool mechanism further includes a spring 130 and a rotation bearing 132. Inner sleeve 118 is coupled with a tool guide, which controls the actuation of tool mechanism 100.

Inner sleeve 118 and outer sleeve 124 exhibit a cylindrical shape. Tool housing 104 also exhibits a cylindrical shape with two prongs extending from the distal base thereof. When tool mechanism 100 is in the assembled and connected state, inner sleeve 118, outer sleeve 124 and tool housing 104 are concentric. The term 'longitudinal direction' or 'longitudinally' relate herein to any direction parallel to the concentric axis of inner sleeve 118, outer sleeve 124 and tool housing 104. The term 'longitudinally move' relates to movement in a longitudinal direction. The term 'actuation' relates herein to the motion (i.e., longitudinal motion, rotation motion) and to the activation of tool 102.

With reference to FIG. 1C, spring 130 applies a force on outer sleeve 124 in the distal direction and each rotation lock teeth $126_1$-$126_5$ is located in one of tool rotation lock grooves $108_1$-$108_5$. Consequently, each rotation lock teeth $126_1$-$126_5$ rotationally lock with two adjacent rotation lock protrusions $106_1$-$106_5$, such that when outer sleeve 124 rotates, tool housing 104, and thus tool 102 rotates as well (i.e., outer sleeve 124 and tool 102 are rotationally locked one with respect to the other). Also, each of sleeve rotation lock pins $120_1$ and $120_2$ of inner sleeve 118 is located in one of sleeve rotation lock grooves $128_1$ and $128_2$ such that when inner sleeve 118 rotates, outer sleeve 124 rotates as well (i.e., inner sleeve 118 and outer sleeve 124 are rotationally locked one with respect to the other). Thus, when inner sleeve 118 rotates, tool housing 104 and thus tool 102 also rotates (i.e., inner sleeve 118 and tool 102 are rotationally locked one with respect to the other). Also, the longitudinal length of sleeve rotation lock grooves $128_1$ and $128_2$ is larger than the longitudinal length of sleeve rotation lock pins $120_1$ and $120_2$, to enable relative motion between outer sleeve 124 and inner sleeve 118 in a longitudinal direction. This relative motion between outer sleeve 124 and inner sleeve 118 is limited by the longitudinal length of sleeve rotation lock grooves $128_1$ and $128_2$, and is equal or larger than the longitudinal length of rotation lock teeth $126_1$-$126_5$.

With reference to FIG. 1D, which depicts tool mechanism 100 in an assembled and connected state with outer sleeve 124 removed, sleeve longitudinal lock pin $122_1$ is inserted into the L-shaped cutout $109_1$, toward the end of the lateral section, such that, in the assembled and connected state, tool housing 104 and inner sleeve 118 do not move one with respect to the other in a longitudinal direction (i.e., tool housing 104 and inner sleeve are longitudinally locked). It is noted that, although not depicted in FIG. 1D, in an assembled and connected state longitudinal lock pin $122_2$ is inserted into the L-shaped cutout $109_2$.

Figure 1E:
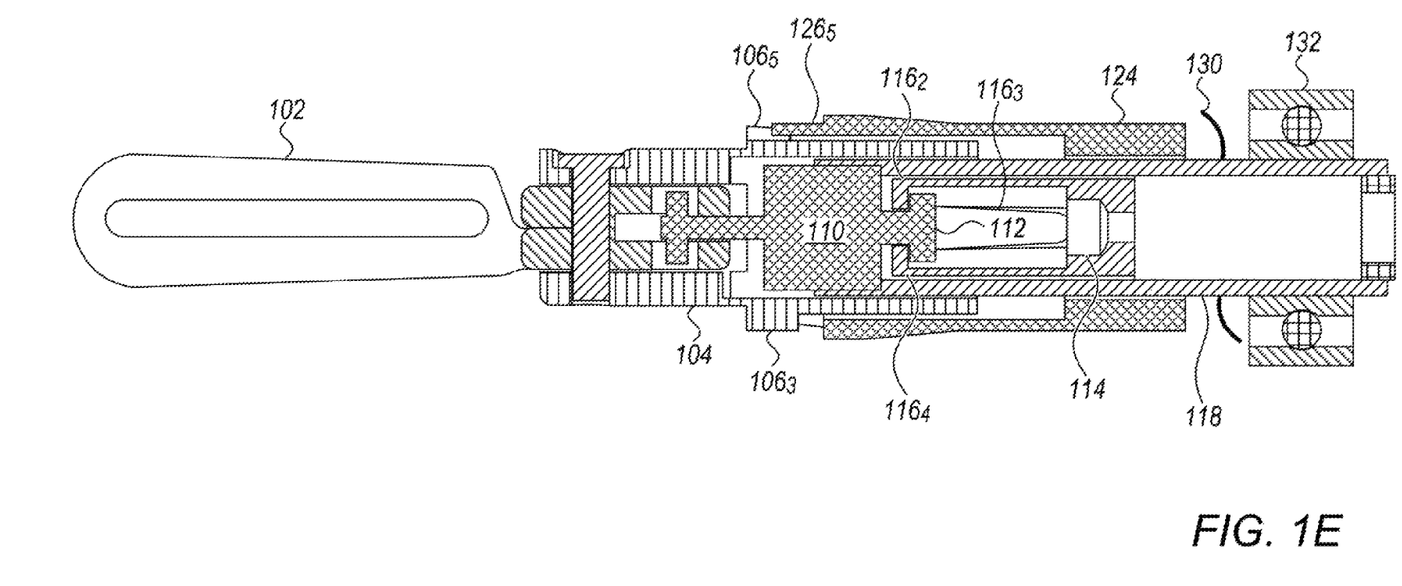

With reference to FIG. 1E, which depicts and cross-section tool mechanism 100 in the assembled connected state, inner sleeve 118 is located over latching spring 114, and presses on spring hooks $116_1$-$116_4$, such that spring hooks $116_1$-$116_4$ latch on mushroom pin 112, and thus on push-pull rod 110. Thus, latching spring 114 is coupled with push-pull rod 110 (i.e., with tool activation interface). It is noted that latching spring 114 and inner sleeve 118 may move independently one with respect to the other in a longitudinal direction.

Figure 1F:
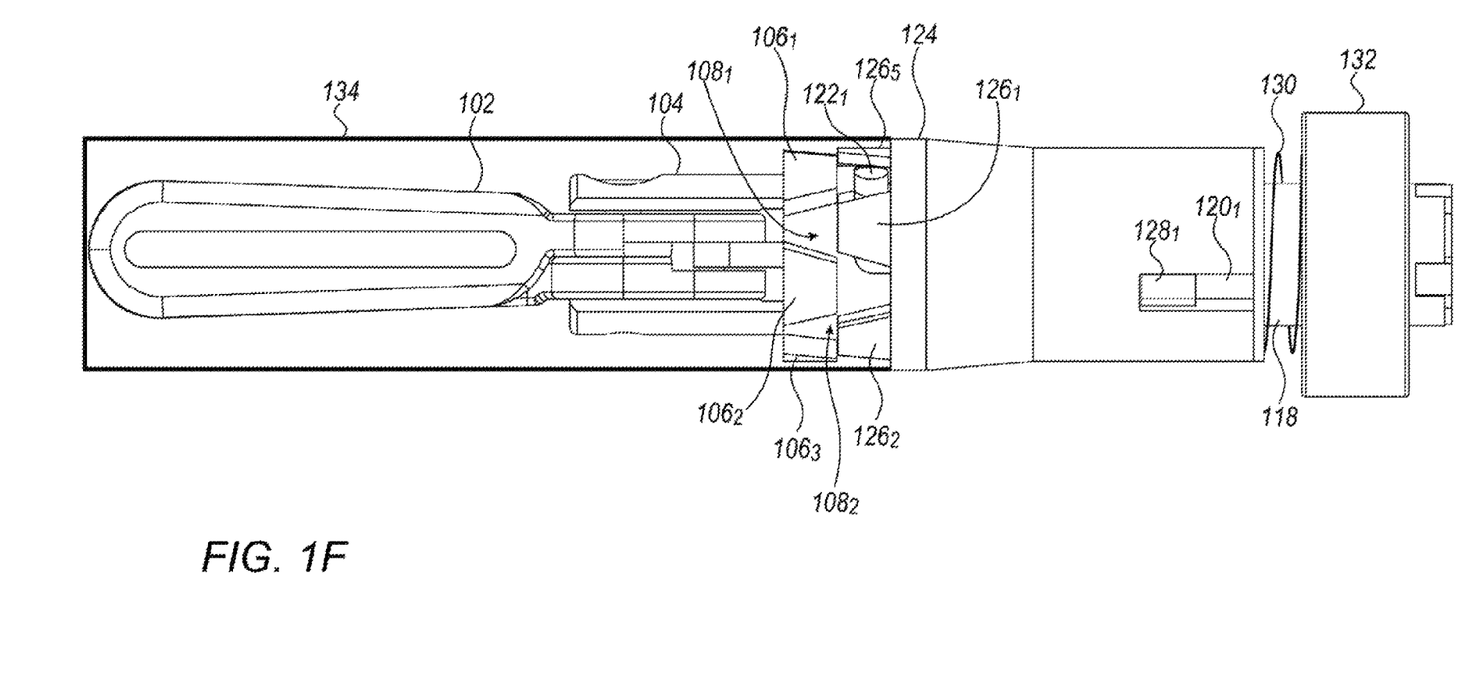
Figure 1G:
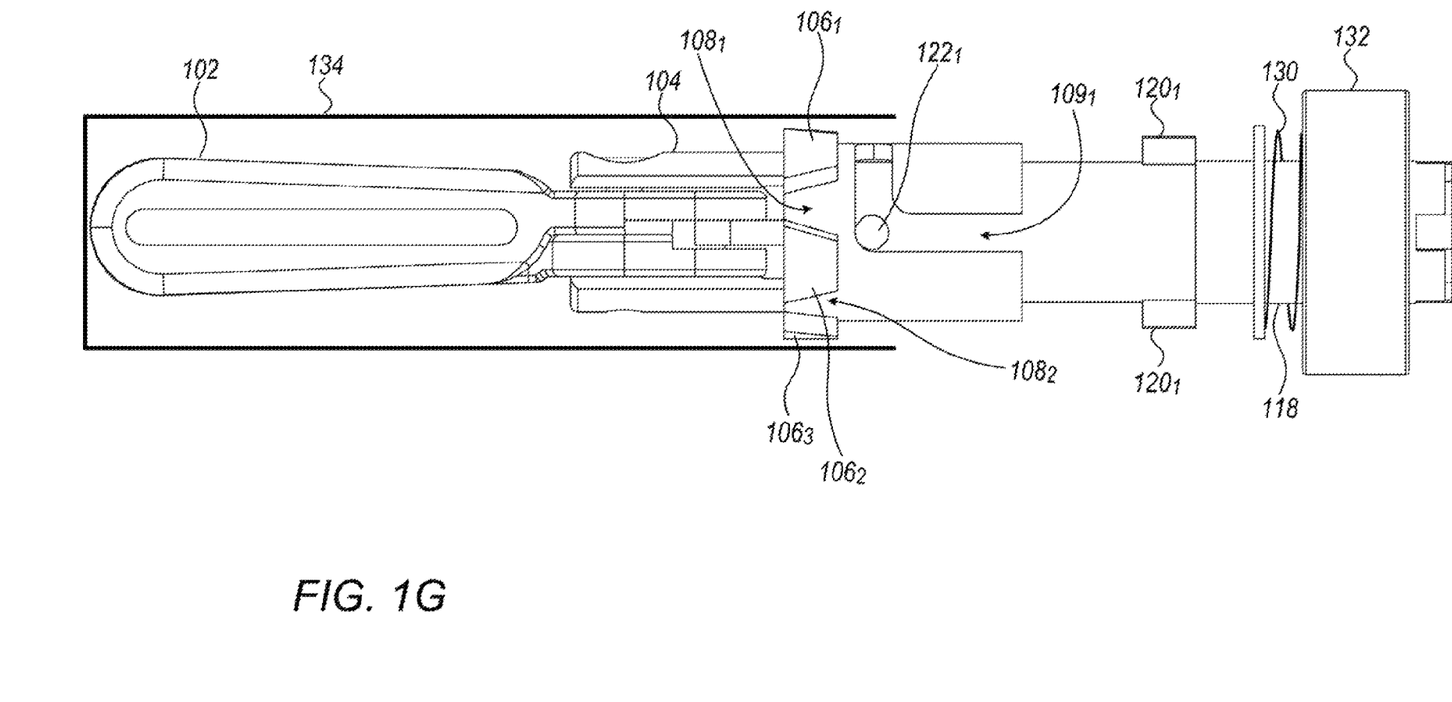
Figure 1H:
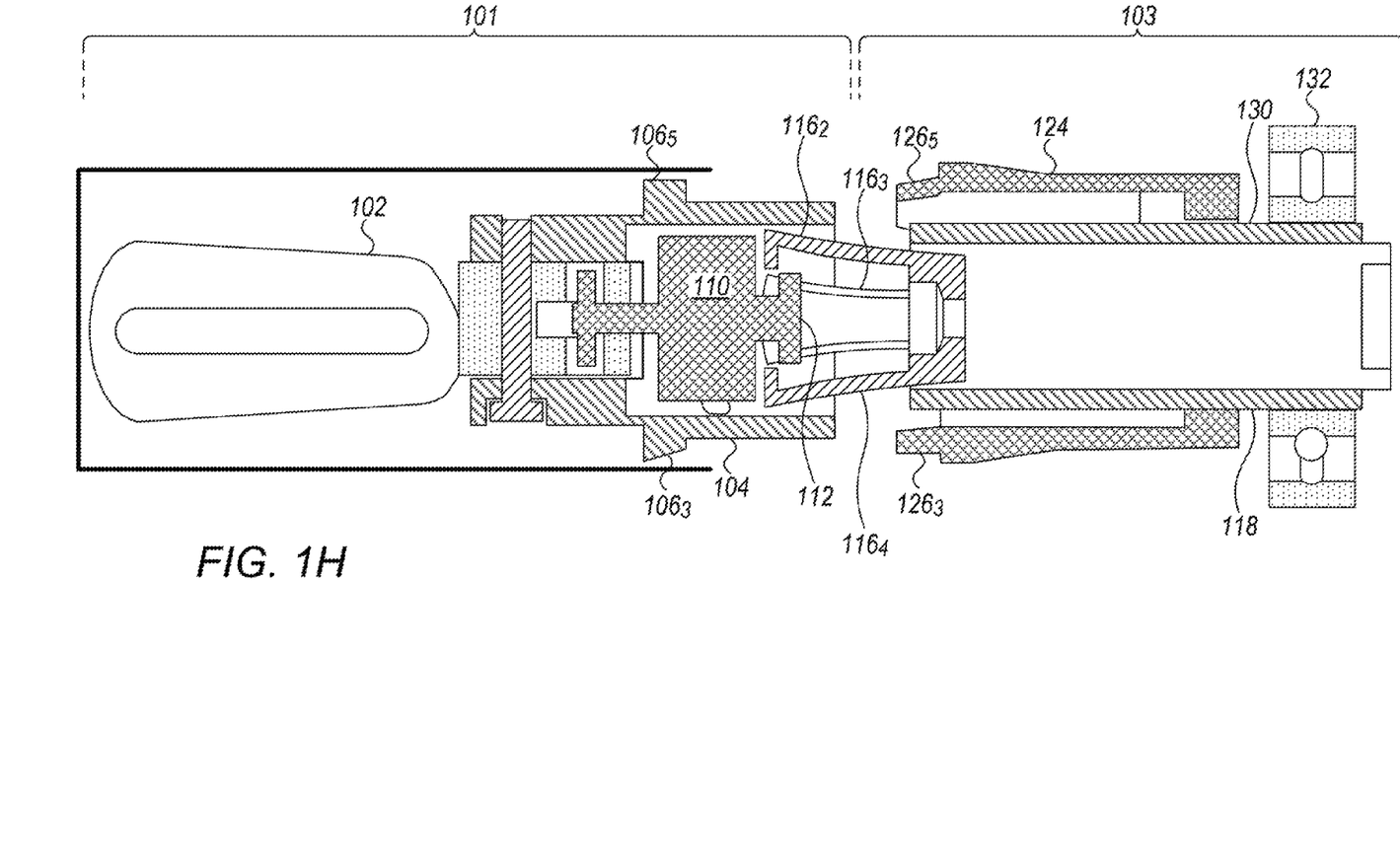
Figure 1I:
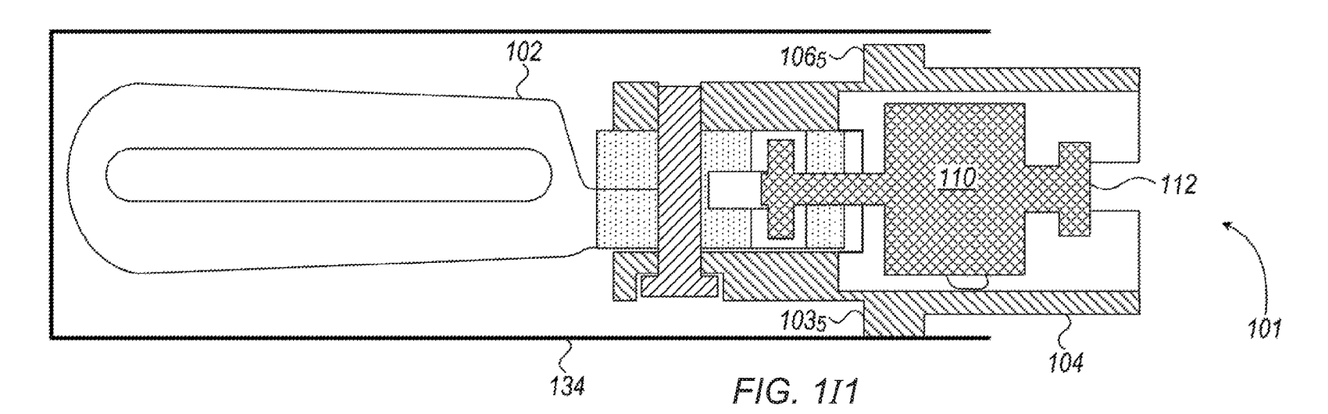
Figures 1I, 1I:
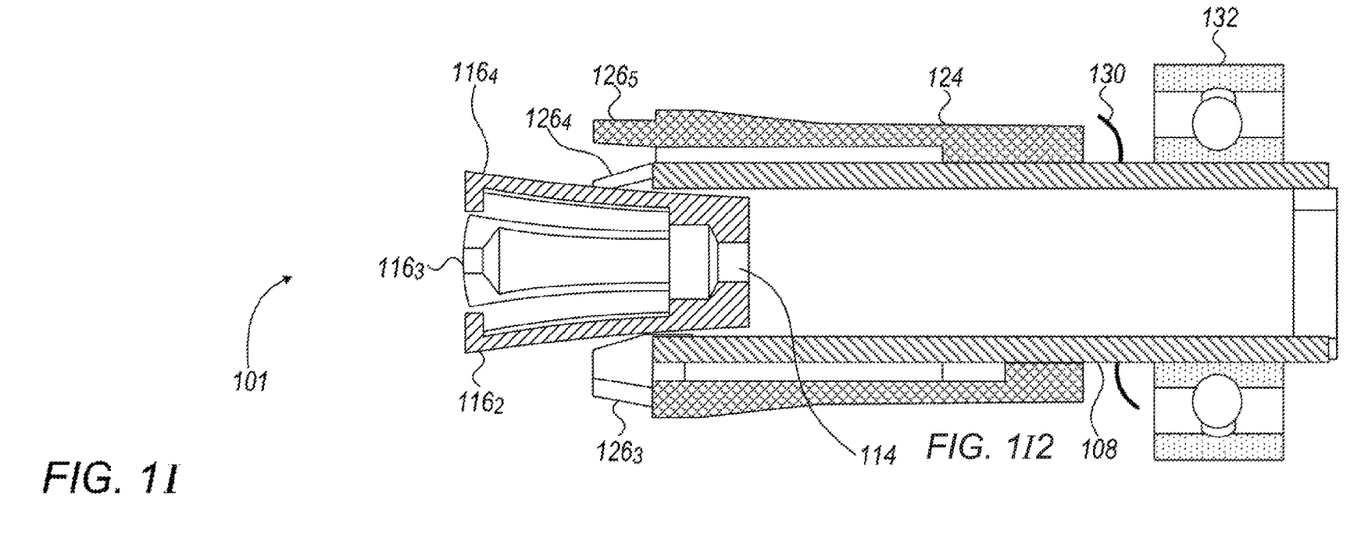

To release of actuation connector 103 from tool section 101, a force is applied on outer sleeve 124 in the proximal direction. With reference to FIG. 1F, as tool mechanism 100 is inserted into a container 134, the rim of container 134 applies a force on outer sleeve 124 in the proximal direction until rotation lock teeth $126_1$-$126_5$ are out of tool rotation lock grooves $108_1$-$108_2$ and outer sleeve 124 is rotationally unlocked from tool housing 104. Thereafter, and with reference to FIG. 1G, inner sleeve 118 is rotated to align longitudinal lock pins $122_1$ and $122_2$ with the longitudinal section of L-shaped cutouts $109_1$ and $109_2$, longitudinally unlocking inner sleeve 118 from tool housing 104 (i.e., inner sleeve and tool housing can longitudinally move one with respect to the other). Thereby, actuation connector 103 is longitudinally unlocked from tool section 101. As inner sleeve 118 rotates, outer sleeve 124 rotates as well. It is noted that, for the sake clarity of the explanation, in FIG. 1G, tool mechanism 100 is depicted with outer sleeve 124 removed. With reference to FIG. 1H, when longitudinal lock pins $122_1$ and $122_2$ are aligned with the longitudinal section of L-shaped cutouts $109_1$ and $109_2$, inner sleeve 118 is pulled toward the proximal direction while the position of latching spring 114 is maintained, to remove inner sleeve 118 from latching spring 114, such that spring hooks $116_1$-$116_4$ release mushroom pin 112. With reference to FIG. 1I, actuation connector 103 is released from tool section 101, and may than connect with a different tool, similar to tool 102.

To connect actuation connector 103 to tool section 101, the above described process is reversed. Actuation connector 103 is position such that spring hooks $116_1$-$116_4$ are located over mushroom pin 112 and the rim containing 134 pushes on outer sleeve 124. Each one of longitudinal lock pins $122_1$ and $122_2$ is aligned with the longitudinal section of one of L-shaped cutouts $109_1$ and $109_2$. Inner sleeve 118 is then pushed over latching spring 114 such that inner sleeve presses on spring hooks $116_1$-$116_4$ and spring hooks $116_1$-$116_4$ latch onto mushroom pin 112. Outer sleeve 124 is then rotated by rotating Inner sleeve 118 until each of rotation lock teeth $126_1$-$126_5$ is aligned with one of tool rotation lock grooves $108_1$-$108_5$. As tool mechanism 100 is extracted from container 134, spring 130 applies a force on outer sleeve 124 in the distal direction such that each one of rotation lock teeth $126_1$-$126_5$ is inserted into one of tool rotation lock grooves $108_1$-$108_5$.

It is noted that container 134 (FIGS. 1A-1I) may be a part of a manifold of containers, where each container is operable to hold a separate tool. In the case of medical surgery, the manifold may be located within the operated cavity (e.g., the abdomen during laparoscopic surgery). The entire tool release and coupling procedures described above occur within the operated cavity. This eliminates the need to insert and/or withdraw the tool from the operated cavity each time a tool is to be changed, as long as the required tool is stored in one of the containers in the manifold. Reference is now made to FIGS. 2A-2D, which are schematic illustrations of a manifold apparatus, generally referenced 200, constructed and operative in accordance with another embodiment of the disclosed technique. Manifold apparatus 200 includes a containers manifold 202 and an arm 204. Manifold 202 includes a distal section 206 and a proximal section 208. Manifold 202 further includes a plurality of containers. In the example depicted in FIG. 2, manifold 202 includes five containers $210_1$, $210_2$, $210_3$, $210_4$ and $210_5$. In each of containers $210_1$-$210_5$, the diameter thereof at the distal section 206 is smaller than the diameter thereof at the proximal section 208. Thus a tool may be inserted completely into one of containers $210_1$-$210_5$, and the rim of the distal section of the container shall apply a force on the outer sleeve of the tool as the tool is pushed into the container. Manifold 202 further includes a plurality of tool passage cavities, such as through tool passage cavities $212_1$, $212_2$ and $212_3$. During operation, various tools, located at the distal end of respective articulation arms, may pass through a respective one of tool passage cavities $212_1$, $212_2$ and $212_3$. For example, and referring to FIG. 2C, at the beginning of the operation, tools $218_1$ and $218_2$, which are located at the distal end of articulation arms $220_1$ and $220_2$ respectively, as well as a camera 214, which is located at the distal end of articulation arm 216, are to be inserted into the operated cavity along with manifold 202. Manifold 202 is inserted into the operated cavity with at least one of containers $210_1$-$210_5$ empty (i.e., to allow storage of the tool being replace). The remaining ones containers $210_1$-$210_5$ include various tools. It is noted that at least each one of articulation arms $220_1$ and $220_2$ includes at the distal end thereof an actuation connector, such as actuation connector 103 described herein above in conjunction with FIGS. 1A-1I). It is also note that at least each one of tools $218_1$ and $218_2$ include a tool activation interface, a longitudinal lock interface and a rotation lock interface as described above in conjunction with FIGS. (1A-1I).

Figure 2A:
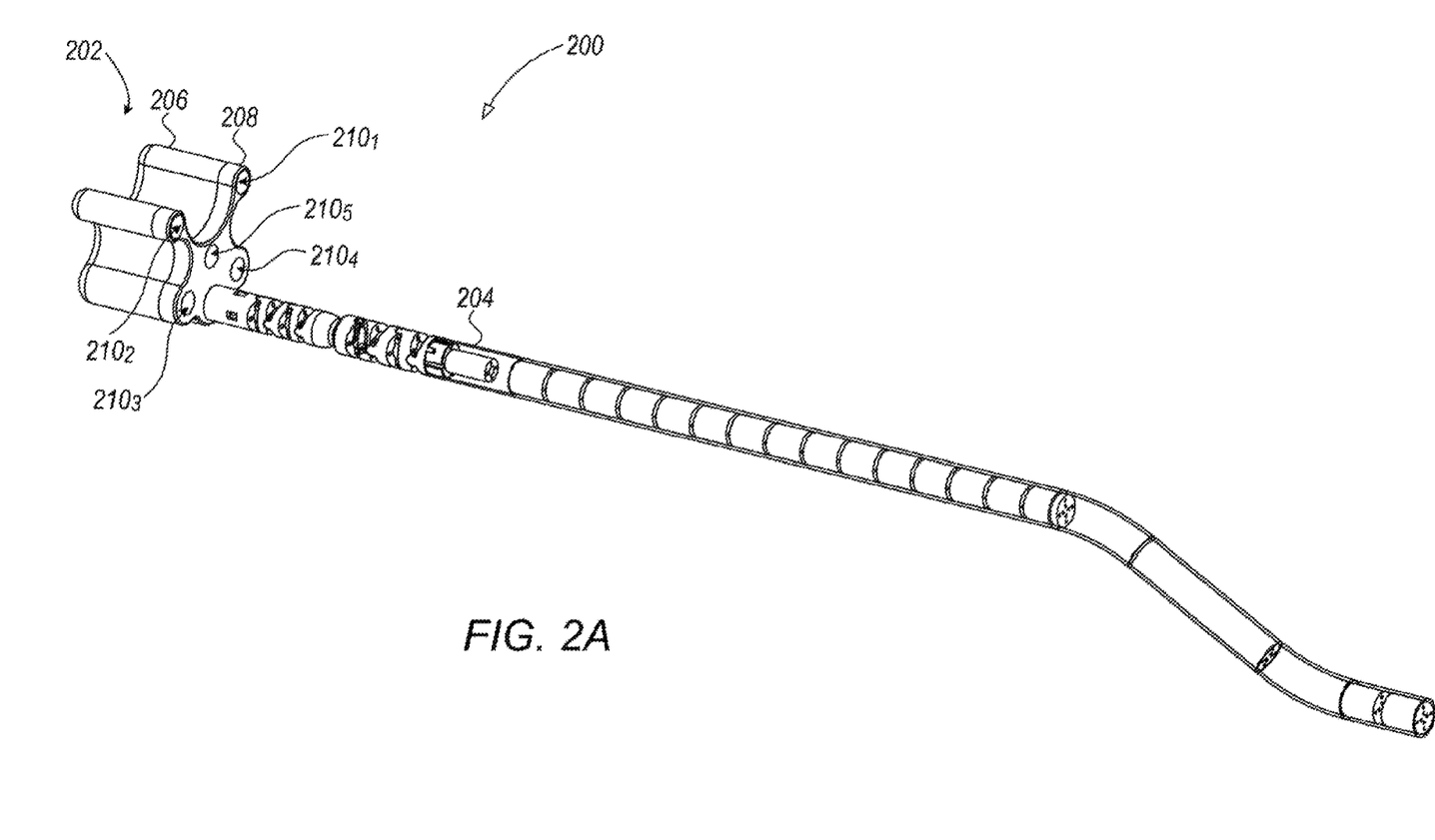
FIGS. 2A-2D are schematic illustrations of a manifold apparatus, constructed and operative in accordance with another embodiment of the disclosed technique.
Figure 2B:
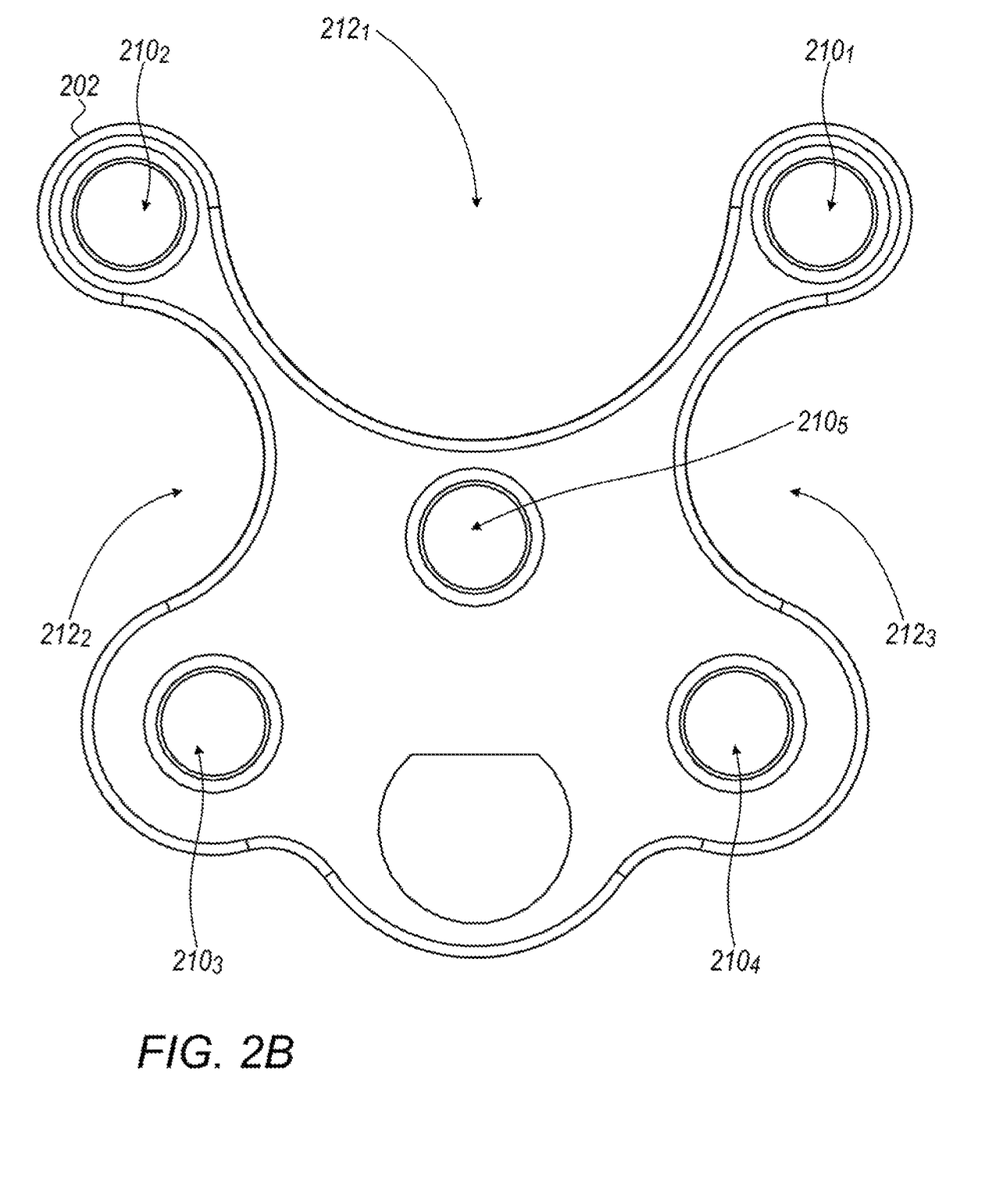
Figure 2C:
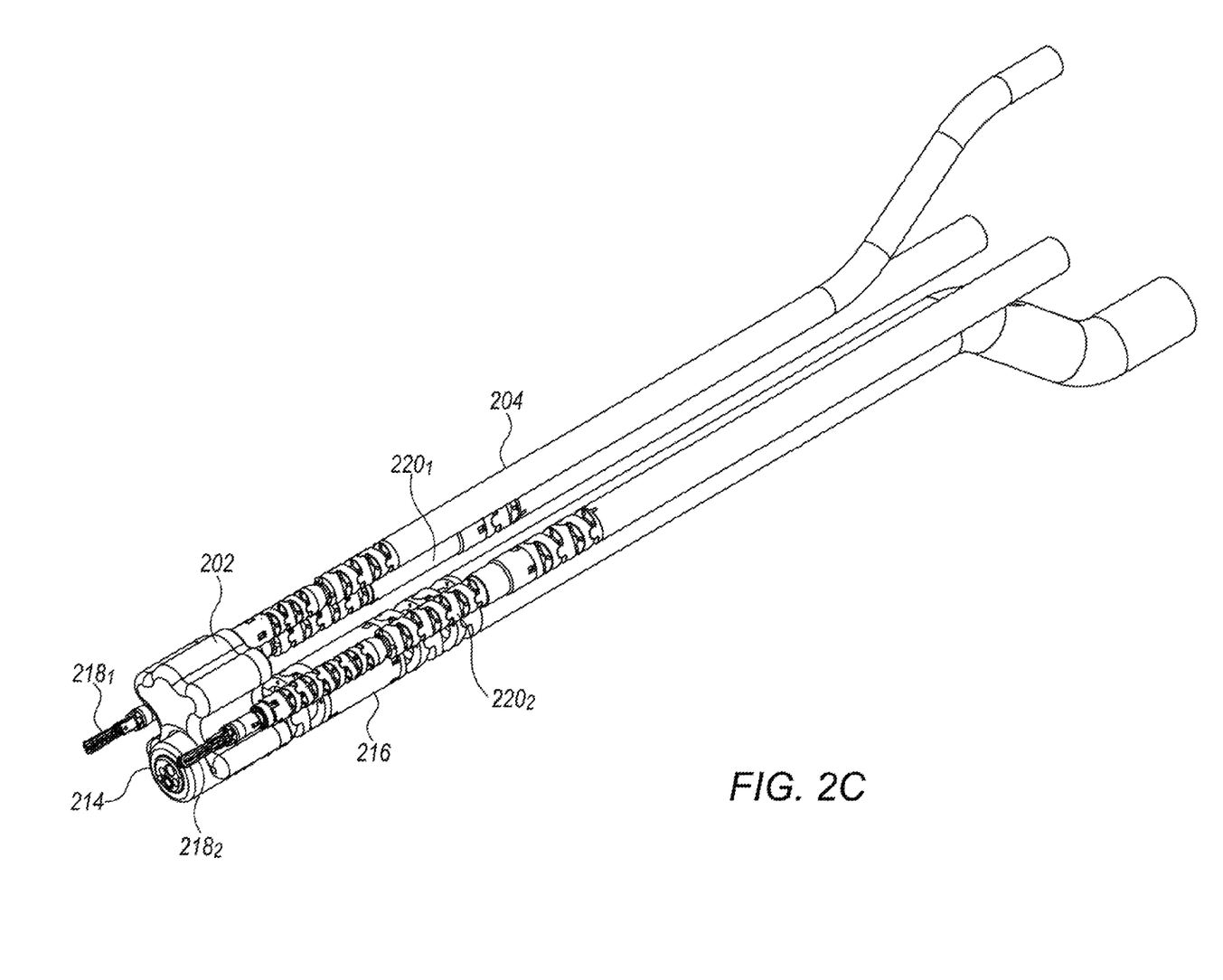
Figure 2D:
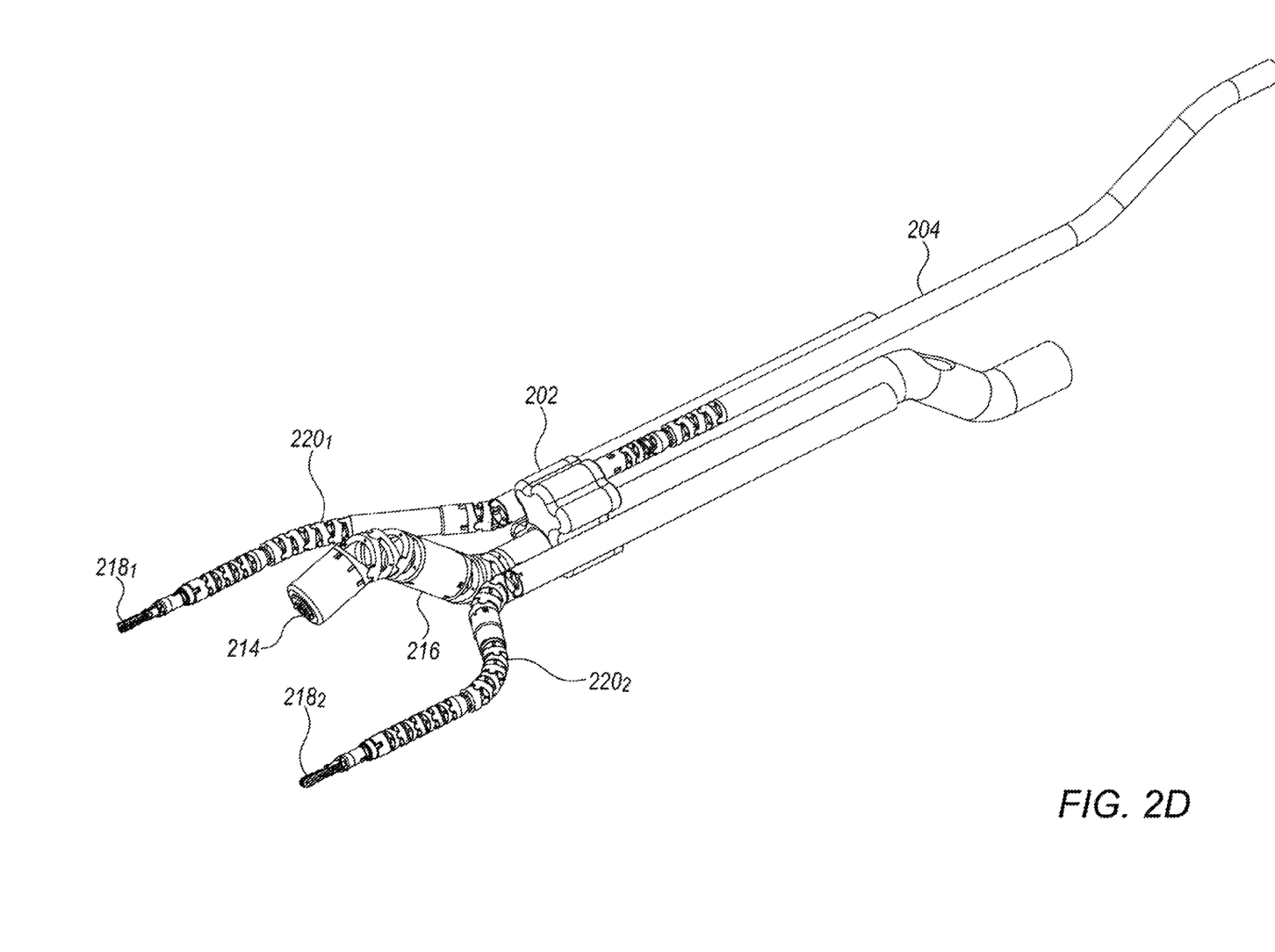

With reference to FIG. 2D, once within the operated cavity, tools $218_1$ and $218_2$ passes through tool passage cavities $212_2$ and $212_3$ respectively and camera 214 passes through tool passage cavity $212_1$. Consequently, tools $218_1$ and $218_2$ may be employed within the operated cavity while camera 214 acquires an image or images of thereof. When a tool is to be replaced, for example, tool $218_1$, then tool $218_1$ is retracted beyond manifold 202. Tool $218_1$ is then aligned with an empty container and released as described above. Articulation arm $220_1$ is then aligned with the selected one of containers $210_1$-$210_5$ (i.e., which stores the required tool) and articulation arm $220_1$ is then coupled with the selected tool as described above. Tool $218_2$ may similarly be exchanged.

It will be appreciated by persons skilled in the art that the disclosed technique is not limited to what has been particularly shown and described hereinabove. Rather the scope of the disclosed technique is defined only by the claims, which follow.

The invention claimed is:

1. An assembly operative to be employed during surgery comprising:
   at least one tool, each of said at least one tool comprising a tool activation interface, a longitudinal lock interface and a rotation lock interface; and
   actuation connector for connecting with each said at least one tool, comprising:
      a latching spring, comprising a plurality of spring hooks, for coupling with said tool activation interface;
      an inner sleeve, operable to longitudinally move relative to said latching spring,
   said inner sleeve coupling said latching spring to said activation interface when said inner sleeve is located over said latching spring and releasing said latching spring from said activation interface when said inner sleeve moves away from said latching spring toward a proximal direction; and
      an outer sleeve, rotationally locked with said inner sleeve, operable to longitudinally move relative to said inner sleeve, said outer sleeve further being operable to rotationally lock with said at least one tool via said rotation lock interface;
   wherein when said actuation connector is connected to said at least one tool, to disconnect said actuation connector from said at least one tool, said outer sleeve is longitudinally moved toward a proximal direction, thereby rotationally unlocking said outer sleeve from said rotation lock interface and thereby rotationally unlocking said actuation connector from said at least one tool;

wherein when said outer sleeve is rotationally unlocked from said rotation lock interface, said inner sleeve is rotated in a first direction, thereby longitudinally unlocking said actuation connector from said at least one tool;

wherein when said actuation connector is disconnected from said tool, to connect said actuation connector to said tool, said inner sleeve is rotated in a second direction different from said first direction, to longitudinally lock said actuation connector with said at least one tool; and wherein, when said inner sleeve is longitudinally locked with said actuation connector, said outer sleeve is longitudinally moved toward a distal direction to rotationally lock with said rotation lock interface, thereby rotationally locking said actuation connector with said at least one tool.

2. The actuation connector according to claim 1, wherein said outer sleeve comprises a plurality of rotation lock teeth; and wherein said rotation lock interface comprises a plurality of tool rotation lock protrusions which create a plurality of tool rotation lock grooves, when said outer sleeve is rotationally locked with said rotation lock interface, each one of said rotation lock teeth is located in one of said tool rotation lock grooves and each one of said rotation lock teeth rotationally lock with two adjacent ones of said rotation lock protrusions.

3. The assembly according to claim 2, wherein said longitudinal lock interface is at least one L-shaped cutout, each of said at least one L-shaped cutout comprising a longitudinal section and a lateral section;

wherein said inner sleeve comprises at least one sleeve longitudinal lock pin; and wherein when each of said at least one sleeve longitudinal lock pin is inserted into one of said at least one L-shaped cutout toward the end of said lateral section, said inner sleeve and said at least tool do not move ene with respect to one another in a longitudinal direction.

4. The assembly according to claim 3, wherein said actuation connector further comprises a spring applying a force on said outer sleeve in a distal direction; and wherein when each one of said rotation lock teeth is aligned with one of said tool rotation lock grooves, each one of said rotation lock teeth is inserted into one of said tool rotation lock grooves.

5. The assembly according to claim 4, wherein when a force is applied on said outer sleeve in the proximal direction, said outer sleeve moves until said rotation lock teeth are out of said tool rotation lock grooves thereby rotationally unlocking said actuation connector from said tool.

6. The assembly according to claim 5, wherein said inner sleeve is rotated to align said at least one longitudinal lock pin with said longitudinal section of said L-shaped cutout thereby longitudinally unlocking said actuation connector from said at least one tool.

7. The assembly according to claim 6, wherein said inner sleeve is pulled toward a distal direction relative to said latching spring to remove said inner sleeve from said latching spring such that said spring hooks are released from said activation interface.

8. The assembly according to claim 1, wherein said inner sleeve comprises at least one sleeve rotation lock pin;

wherein said outer sleeve comprises at least one sleeve rotation lock groove; and wherein each of said at least one sleeve rotation lock pin is located in one of said at least one sleeve rotation lock groove.

9. The assembly according to claim 1 further comprising a manifold apparatus operative for containing medical tools during operation, said manifold apparatus comprising:

a containers manifold comprising a plurality of tool containers, for containing medical tools, said containers manifold further comprising an at least one tool passage cavity operative to enable at least one arm with said at least one tool attached thereto to pass through a respective one of said at least one tool passage cavity, toward an operated region; and a manifold arm comprising articulation links, coupled with said containers manifold, operative to maneuver said containers manifold.

10. The assembly according to claim 9, wherein said containers manifold comprises a proximal section and a distal section, and wherein a diameter of each container of said plurality of tool containers at said distal section is smaller than a diameter of each container of said plurality of tool containers at said proximal section.

11. The assembly according to claim 9, wherein at least one of said plurality of tool containers is empty during surgery.

12. The assembly according to claim 11, wherein at least one of said plurality of tool containers comprises at least a second tool.

13. An actuation connector for connecting with a tool, said tool comprising a tool activation interface, a longitudinal lock interface and a rotation lock interface, said actuation connector comprising:

a latching spring, comprising a plurality of spring hooks, for coupling with said tool activation interface;

an inner sleeve, operable to longitudinally move relative to said latching spring, said inner sleeve coupling said latching spring to said activation interface when said inner sleeve is located over said latching spring and releasing said latching spring from said activation interface when said inner sleeve moves away from said latching spring toward a proximal direction;

an outer sleeve, rotationally locked with said inner sleeve, operable to longitudinally move relative to said inner sleeve, said outer sleeve further being operable to rotationally lock with said tool via said rotation lock interface;

wherein when said actuation connector is connected to said tool, to disconnect said actuation connector from said tool, said outer sleeve is longitudinally moved toward a proximal direction, thereby rotationally unlocking said outer sleeve from said rotation lock interface and thereby rotationally unlocking said actuation connector from said tool;

wherein when said outer sleeve is rotationally unlocked from said rotation lock interface, said inner sleeve is rotated in a first direction, thereby longitudinally unlocking said actuation connector from said tool;

wherein when said actuation connector is disconnected from said tool, to connect said actuation connector to said tool, said inner sleeve is rotated in a second direction different from said first direction, to longitudinally lock said actuation connector with said tool; and wherein, when said inner sleeve is longitudinally locked with said actuation connector, said outer sleeve is longitudinally moved toward a distal direction to rotationally lock with said rotation lock interface, thereby rotationally locking said actuation connector with said tool.

14. The actuation connector according to claim 13, wherein said outer sleeve comprises a plurality of rotation lock teeth; and wherein said rotation lock interface comprises a plurality of tool rotation lock protrusions which create a plurality of tool rotation lock grooves, when said outer sleeve is rotationally locked with said rotation lock interface, each one of said rotation lock teeth is located in one of said tool rotation lock grooves and each one of said rotation lock teeth rotationally locks with two adjacent ones of said rotation lock protrusions.

15. The actuation connector according to claim 14, wherein said longitudinal lock interface is at least one L-shaped cutout, each one of said at least one L-shaped cutout comprising a longitudinal section and a lateral section;

wherein said inner sleeve comprises at least one sleeve longitudinal lock pin; and wherein when each of said at least one sleeve longitudinal lock pin is inserted into one of said at least one L-shaped cutout toward the end of said lateral section, said inner sleeve and said tool do not move with respect to one another in a longitudinal direction.

16. The actuation connector according to claim 15, wherein said actuation connector further comprises a spring, for applying a force on said outer sleeve in the distal direction; and wherein when each of said rotation lock teeth is aligned with one of said tool rotation lock grooves, each one of said rotation lock teeth is inserted into one of said tool rotation lock grooves.

17. The actuation connector according to claim 16, wherein when a force is applied on said outer sleeve in the proximal direction, said outer sleeve moves until said rotation lock teeth are out of said tool rotation lock grooves thereby rotationally unlocking said actuation connector from said tool.

18. The actuation connector according to claim 17, wherein said inner sleeve is rotated to align said at least one longitudinal lock pin with said longitudinal section of said L-shaped cutout thereby longitudinally unlocking said actuation connector from said tool.

19. The actuation connector according to claim 18, wherein said inner sleeve is pulled toward a distal direction relative to said latching spring to remove said inner sleeve from said latching spring such that said spring hooks are releases from said activation interface.

20. The actuation connector according to claim 13, wherein said inner sleeve comprises at least one sleeve rotation lock pin, wherein said outer sleeve comprises at least one sleeve rotation lock groove, and wherein each of said at least one sleeve rotation lock pin is located in one of said at least one sleeve rotation lock groove.

* * * * *